United States Patent
Enomoto et al.

[11] Patent Number: 5,646,007
[45] Date of Patent: Jul. 8, 1997

[54] METHOD FOR DETERMINATION OF ANTITHROMBIN III ACTIVITY AND REAGENT KIT THEREFOR

[75] Inventors: Masayasu Enomoto, Takatsuki; Haruhiko Nishimura, Osaka, both of Japan

[73] Assignee: Nippon Shoji Kaisha Ltd., Osaka, Japan

[21] Appl. No.: 381,882

[22] PCT Filed: Jun. 27, 1994

[86] PCT No.: PCT/JP94/01024

§ 371 Date: Feb. 17, 1995

§ 102(e) Date: Feb. 17, 1995

[87] PCT Pub. No.: WO95/00663

PCT Pub. Date: Jan. 5, 1995

[30] Foreign Application Priority Data

Jun. 28, 1993 [JP] Japan ................... 5-157001

[51] Int. Cl.$^6$ ................ C12Q 1/56; C12Q 1/00; G01N 33/53; G01N 33/48
[52] U.S. Cl. ................ 435/13; 435/4; 435/810; 435/975; 435/7.95; 436/63; 436/69; 436/74
[58] Field of Search ................ 435/13, 4, 810, 435/975, 7.95, 63, 69, 74

[56] References Cited

U.S. PATENT DOCUMENTS

| | | | |
|---|---|---|---|
| 4,473,639 | 9/1984 | Sommer et al. | 435/13 |
| 4,736,018 | 4/1988 | Reutelingsperger | 435/13 |
| 4,918,001 | 4/1990 | Kolde | 435/24 |
| 4,948,724 | 8/1990 | Yin | 435/13 |
| 5,093,237 | 3/1992 | Enomoto | 435/13 |
| 5,221,614 | 6/1993 | Enomoto | 435/13 |
| 5,248,596 | 9/1993 | Esmon et al. | 435/13 |
| 5,320,945 | 6/1994 | Dessauer et al. | 435/13 |

OTHER PUBLICATIONS

Abildgaard et al., "Antithrombin (Heparin Cofactor) Assay with New Chromogenic Substrates (s–2238 and Chromozyn TH)", Thrombosis Research, vol. 11, 1977, pp. 549–553.

M. Ukita, "ATIII, Heparin", Clinichopathologic, Rinsyo Byori, Special, vol. 70, 1987, pp. 173–180, with full English transistion.

M. Enomoto et al., "Antithrombin–III Assay without Influence of Heparin Cofactor II", Thrombosis Research, vol. 57, 1990, pp. 729–736.

K. Takahashi et al., Rinsho Byori, Special vol. 70, 1987, pp. 181–186.

D. Tollefsen et al., "Activation of Heparin Cofactor II by Dermatan Sulfate", Jour. Biological Chemistry, vol. 258, No. 11, 1983, pp. 6713–6716.

D. Tollefsen et al., "Heparin Cofactor II", Jour. Biological Chemistry, vol. 257, No. 5, 1982, pp. 2162–2169.

F. Church et al., "Antithrombin Activity of Fucoidan", Jour. Biological Chemistry, vol. 264, No. 6, 1989, pp. 3618–3632.

J. Conard et al., "Bovine or Human Thrombin in Amidolytic AT III Assays", Thrombosis Research, vol. 41, 1986, pp. 873–878.

*Primary Examiner*—John Kight
*Assistant Examiner*—Louise Leary
*Attorney, Agent, or Firm*—Foley & Lardner

[57] ABSTRACT

An improved method of a conventional antithrombin III activity determination method, which does not require dilution of a sample and can avoid influence of heparin cofactor II is provided. This method is characterized in that the reaction of a sample with thrombin in the presence of heparin is carried out in the presence of more than 0.2 to 0.9M of a salt, while such a reaction is carried out in the presence of 0.2M of a salt in a conventional method.

14 Claims, 3 Drawing Sheets

METHOD FOR DETERMINATION OF ANTITHROMBIN III ACTIVITY AND REAGENT KIT THEREFOR

INDUSTRIAL FIELD OF APPLICATION

The present invention relates to a method for the determination of antithrombin III (hereinafter abbreviated as ATIII) activity in body fluids. More specifically, it relates to an improved method for the determination of ATIII activity in body fluids comprising reacting a sample with thrombin in the presence of heparin and a salt and then measuring a color developed from a chromogenic substrate to determine the remaining thrombin activity. The present invention further relates to a reagent kit to be used in the method for the determination of ATIII activity.

PRIOR ART AND PROBLEMS

ATIII is a serine protease inhibitor present in blood in a large amount (20 to 30 mg/dl) and is known as a blood coagulation inhibitor. Blood coagulation takes place by an amplification reaction due to cascade-like function of many proteases. In the final stage of blood coagulation, thrombin thus formed converts fibrinogen into fibrin and, in addition, thrombin activates blood coagulation factor XIII. The activated blood coagulation factor XIII forms crosslinkages between fibrins to form thrombi. A most important regulator of this formation of thrombi is ATIII and ATIII binds to thrombin and proteases which participate in blood coagulation such as blood coagulation factor X and the like to inhibit them. When ATIII in blood is lowered, thrombi are liable to be formed. Therefore, lowering of ATIII in blood causes trouble. It has been known that lowering of ATIII in blood occurs by, for example, low nutriture, severe hepatic diseases, coagulation sthenia such as diffuse intravascular coagulation (DIC), acute thrombosis and the like, nephrotic syndrome, and congenital ATIII deficiency or abnormality. Then, ATIII is an important indication in clinical diagnosis.

As methods for the determination of ATIII, immunological methods for the determination of immunizing doses, methods using fibrinogen or chromogenic substrates, and methods using ATIII deficient plasma containing coagulation factors participating in extrinsic reactions have already been known. We have invented a method using ATIII deficient plasma containing coagulation factors participating in extrinsic reactions (PCT/JP89/00173 (Nov. 2, 1989); and Thrombosis Research, Vol. 57, 729–736 (1990)). In this method, ATIII can be simply, easily and accurately determined by measuring a blood coagulation time with minimum influence of heparin cofactor II (hereinafter abbreviated as HCII). However, since a blood coagulation time is measured in this method, it is difficult to apply the method to general automatic analyzers.

At present, methods using chromogenic substrates are widely used because they are readily applicable to automatic analyzers.

In a method using a chromogenic substrate, an excess amount of thrombin is added to a sample to react ATIII in the sample with thrombin in the presence of heparin and a salt and then a chromogenic substrate is added to the reaction mixture to measure a color developed to determine the remaining thrombin activity, that is, to indirectly determine ATIII in the sample. This determination of ATIII is described by, for example, Rinsho Byori, Special Vol. 70, 173–177 (1987); U. Abildgaard, et al., Thrombosis Research, Vol. 11, 549–553 (1977).

In this method for the determination of ATIII with a chromogenic substrate, there are two major problems. One problem is dilution of a sample. In general, it is necessary to dilute a sample so as to avoid influence of its inherent color and turbidity upon measurement. In addition, since a sample contains a large amount of ATIII, when the sample is used without any dilution, a very large amount of thrombin must be added because the amount of thrombin should exceed the amount of ATIII. In such a case, since 0% of ATIII activity corresponds to the activity of thrombin added for preparing a calibration curve, a color released from a chromogenic substrate reaches a measurable limit of absorbance within a very short period of time. For applying to various automatic analyzers, it is undesirable to exceed 2.0 of absorbance within an extremely short period of time, e.g., within one minute. Although influence of an inherent color and turbidity of a sample upon measurement can be avoided by carrying out a kinetic analysis, the problem that the color released reaches a measurable limit of absorbance within a very short time still remains. Dilution of samples are very inconvenient for routine tests. For solving this problem, it has been proposed to use an oligopeptide substrate which has a 1/5 to 1/100 times lower sensitivity to thrombin in comparison with Tos-Gly-Pro-Arg-pNA as a substrate in the presence of a denaturant or tetrapeptide, Gly-Pro-Arg-Pro (U.S. Pat. No. 5,320,945) (Jul. 14, 1994)

Another problem is to avoid the influence of HCII because ATIII determination is influenced by HCII. HCII is present in an amount of about 9 mg/dl in normal plasma and is about 1/3 of ATIII. Although HCII inhibits thrombin as ATIII does, unlike ATIII, HCII does not inhibit other coagulation factors. Like ATIII, antithrombin activity of HCII is remarkably enhanced by addition of heparin. However, it has been known that the optimum concentration of heparin is 1 to 5 U/ml and this is higher than that for ATIII (0.1 to 1 U/ml) and, in addition, activation manners by other sulfated polysaccharides are different from each other (Rinsho Byori, Special Vol. 70, 181–186 (1987); and Douglas M. Tollersen et al., The Journal of Biological Chemistry, Vol. 258, No. 11, 6713–6716 (1983)). In addition, regarding affinity for heparin, HCII is weaker than ATIII. For example, after bonding to a heparin-Sepharose column, HCII can be eluted with 0.12 to 0.16M sodium chloride, while ATIII is first eluted with 0.4M or more sodium chloride (Douglas M. Tollefsen et al., The Journal of Biological Chemistry, Vol. 257, No. 5, 2162–2169 (1982)). In connection with this heparin affinity, the rate of inhibition of thrombin by HCII in the presence of heparin has been known to depend on ionic strength (Frank C. Church et al., The Journal of Biological Chemistry, Vol. 264, No. 6, 3618–3623 (1989)). Regarding the influence of HCII on the determination of ATIII, there is described that the influence of HCII can be avoided by using bovine thrombin instead of human thrombin (Jacqueline Conard et al., Thrombosis Research, Vol. 41, 873–878 (1986)).

However, according to the method for determination of ATIII described in Rinsho Byori, Special Vol. 70, 173–177 (1987) and U. Abildgaard et al., Thrombosis Research, Vol. 11, 549–553 (1977), we have confirmed that, even if bovine thrombin is used, HCII greatly influences at the salt concentration of 0.2M which is usually employed in a known method and is higher than the salt concentration at which, according to the above literature, HCII loses affinity for heparin.

As described above, since known methods for the determination of ATIII activity have the problem that it is influenced by HCII, an object of the present invention is to solve this problem. In addition, upon determination of ATIII, a sample should be diluted. If a sample is not diluted, a large excess amount of thrombin should be used, which results in the problem that an absorbance exceeds a measurable limit within a very short period of time. Another object of the present invention is therefore to solve this problem so that the determination is readily applicable to an automatic analyzer and thereby a simple, easy and accurate determination method and a reagent can be provided.

MEANS FOR SOLVING THE PROBLEMS

Figure 1:
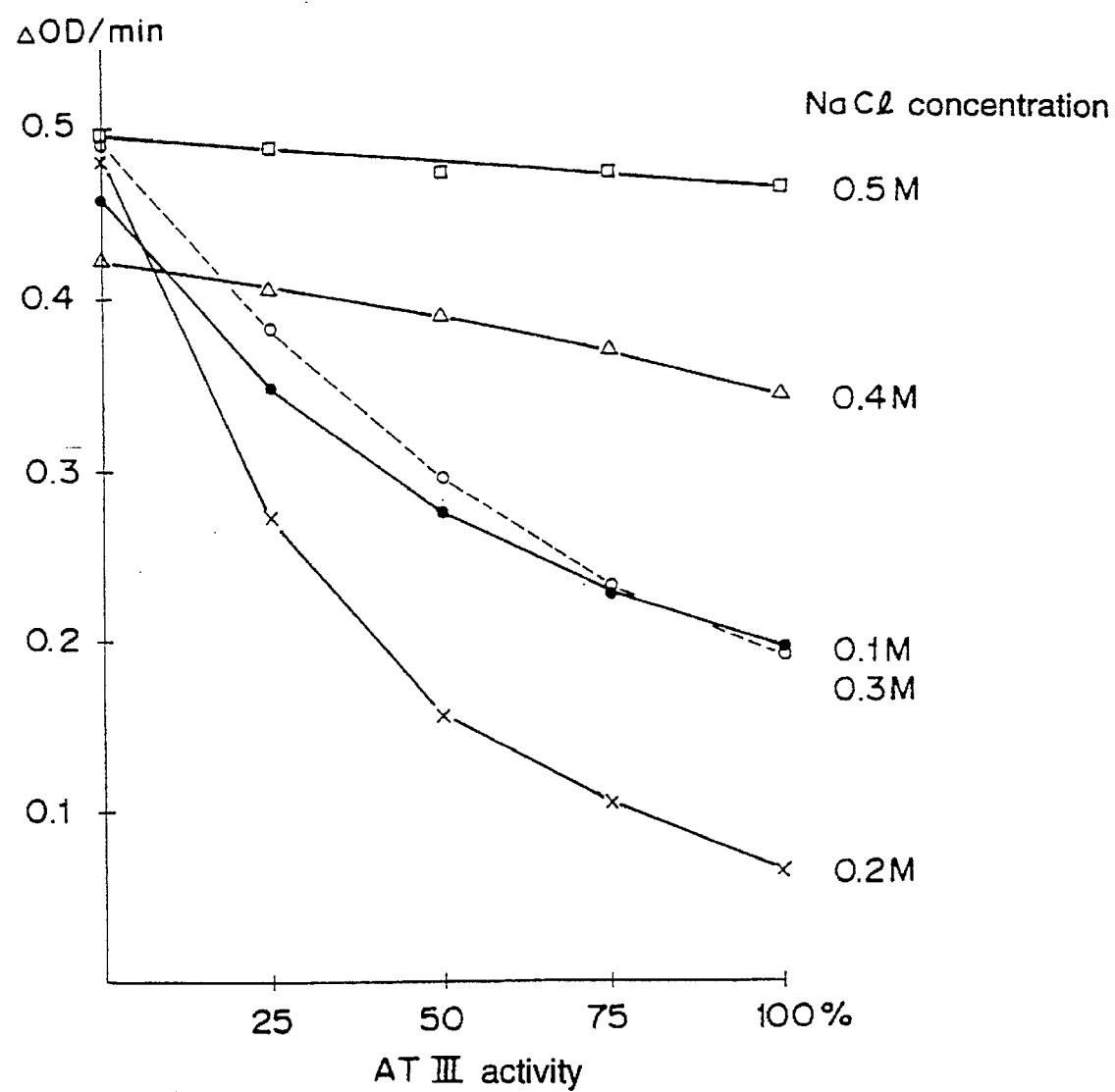
FIG. 1 is a graph showing a calibration curve of ATIII activity at the salt concentration of 0.10 to 0.50M according to the method of U.S. Pat. No. 4,918,001 (Apr. 17, 1990) described in Reference Example hereinafter.

The present inventors have studied intensively to solve the above-described problems. As a result, it has been unexpectedly found that the above problems can be solved by using a higher concentration of a salt in a reaction mixture in a method for the determination of ATIII activity comprising adding thrombin to a sample, allowing to react them in the presence of heparin and a salt, and then, after the reaction, measuring a remaining thrombin activity by using a chromogenic substrate. Thus, the present invention has been completed.

That is, according to the present invention, there is provided a method for the determination of antithrombin III activity which comprises adding a given excess amount of thrombin to a sample, reacting them in the presence of heparin and a salt, and then measuring a remaining thrombin activity with a chromogenic substrate which develops a color by the reaction with thrombin, the concentration of said salt being more than 0.20M to not more than 0.90M, preferably, not less than 0.25M to 0.60M, more preferably, not less than 0.35M to 0.60M.

In a known method, a salt concentration in the reaction of a sample with thrombin in the presence of heparin is 0.2M. However, in the present invention, the influence of HCII can be avoided by such a very simple and less expensive means as the increase in the salt concentration. In addition, in the present invention, the amount of thrombin to be used can be reduced and thereby dilution of a sample is not required. Thus, the present invention provides such advantage that ATIII can be simply, easily and accurately determined, without dilution of a sample and exceeding a measurable limit within a short period of time, and the method is readily applicable to automatic analyzers.

Namely, firstly, as the salt concentration in the reaction mixture of a sample and thrombin increased, the influence of HCII decreased. More specifically, about 40% of the influence was avoided at the salt concentration of 0.22M, about 60% of the influence was avoided at the salt concentration of 0.24M, about 90% of the influence was avoided at the salt concentration of 0.26M and no influence was observed at the salt concentration of not less than 0.3M (Example 2). Then, in the determination of ATIII with thrombin having a certain constant activity and a given amount of a sample (Example 3), up to the salt concentration of 0.3M, about 90% of thrombin was inhibited at 100% of ATIII activity and the linearity of a calibration curve was maintained up to 75% of ATIII activity, while, as to the salt concentration of 0.4M, about 50% of thrombin was inhibited at 100% of ATIII activity and the linearity of calibration curve was maintained up to 100% of ATIII activity. As to the salt concentration of 0.5M, about 15% of thrombin was inhibited at 100% of ATIII activity. This suggests that more amount of a sample can be tested and/or thrombin activity to be added as the reagent can be further reduced. By decreasing the amount of thrombin to be added as the reagent, another problem that the absorbance exceeds a measurable limit within a short period of time can be solved.

Figure 2:
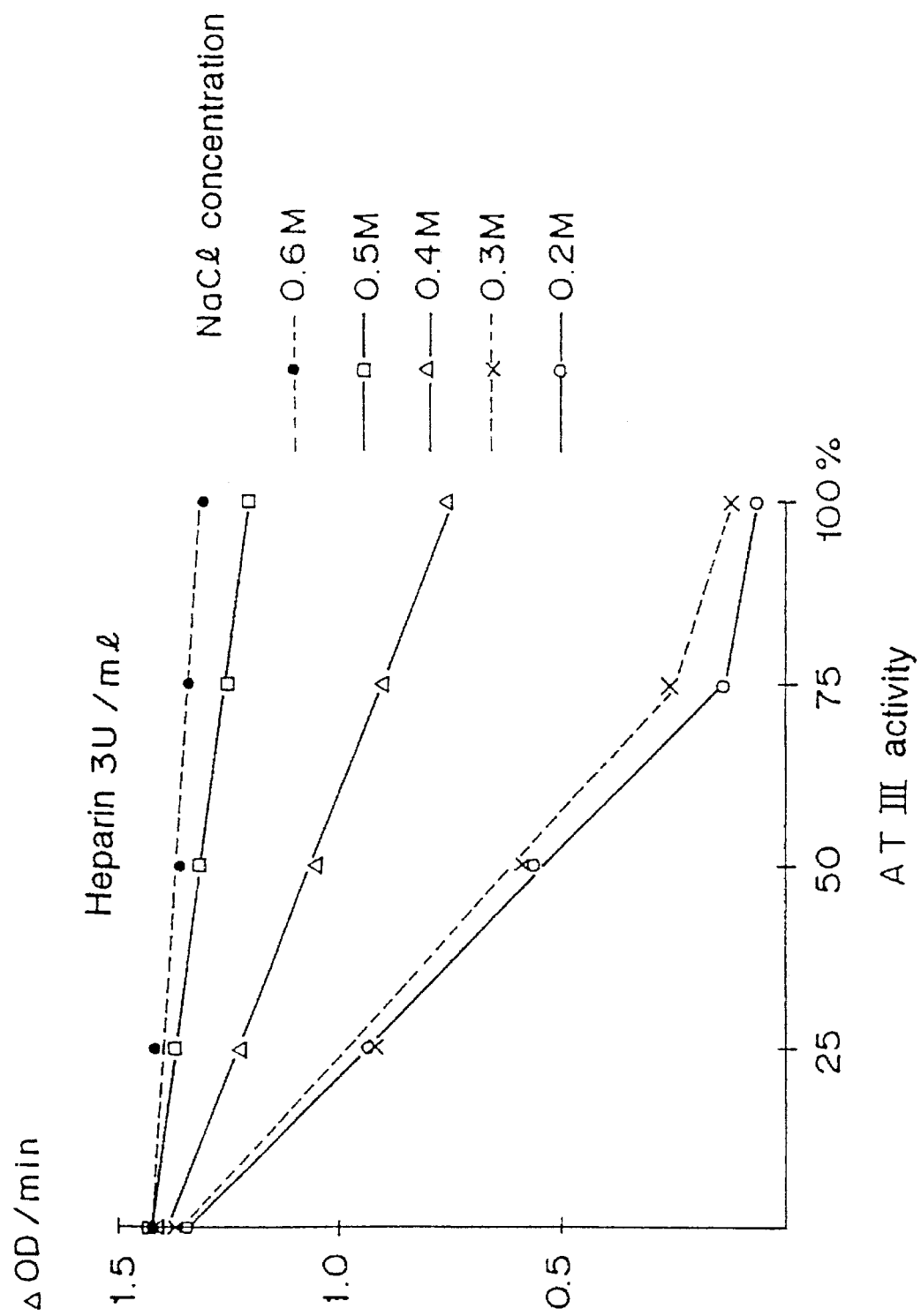
FIG. 2 is a graph showing a calibration curve of ATIII activity at the salt concentration of 0.20 to 0.60M in a thrombin reagent (heparin concentration: 3 U/ml) described in Example 3 hereinafter.
Figure 3:
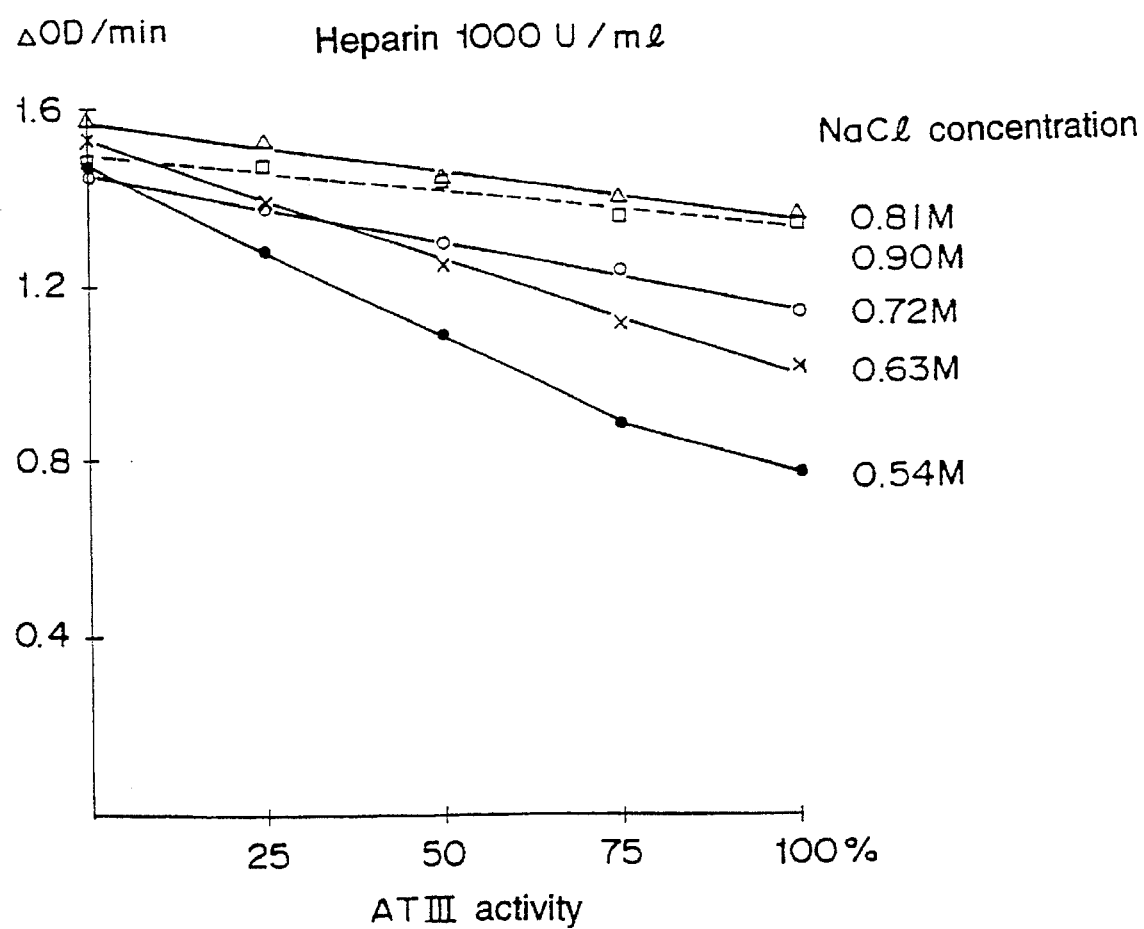
FIG. 3 is a graph showing the relationship between salt concentrations and a calibration curve of ATIII at heparin concentration of 1,000 U/ml described in Example 4 hereinafter.

Furthermore, in the calibration curve (FIG. 2) prepared under determination conditions of Example 3 (heparin concentration in the reaction mixture: 3 U/ml), although the sensitivity at the salt concentration of not less than 0.5M is not preferred, it has been found that the sensitivity can be improved by increasing the amount of heparin (Example 4, FIG. 3).

Thus, it has been found that the preferred sensitivity can be obtained without dilution of a sample and exceeding a measurable limit of absorbance within a short period of time by suitably selecting the amount of a sample, thrombin activity, the salt concentration and the amount of heparin. At the same time, the influence of HCII can be avoided. In the present invention, the reaction time course is linear, the calibration curve maintains good linearity, and reproducibility is good. Therefore, the method of the present invention is suitable for using as routine tests.

When the method of the present invention is compared to conventional methods, U.S. Pat. No. 5,320,945 (Jul. 14, 1994) merely proposes a chromogenic substrate which has a low sensitivity to thrombin and there is no description of a salt concentration. No consideration is given for avoiding the influence of HCII which is one of major problems in the determination of ATIII. In this respect, the proposal is different from the method of the present invention.

U.S. Pat. No. 4,918,001 (Apr. 17, 1990) proposes a method for the determination of protease inhibitors, wherein a sample and a substrate are mixed, a protease is added to the mixture to start their reaction and then a hydrolyzing rate of the substrate is measured. In this method, ATIII is also determined and the addition of a neutral salt, preferably, sodium chloride in a concentration of 0 to 0.5M, preferably, 0.08 to 0.15M is described. This method is different from conventional methods for the determination of ATIII in that the substrate is added prior to addition of thrombin and no pre-heating and pre-dilution of a sample are required.

In fact, when the determination of ATIII was carried out at the salt concentration in a thrombin reagent of 0.1 to 0.5M according to the method as Example 1 of U.S. Pat. No. 4,918,001 (Apr. 17, 1990), the calibration curve was prepared (FIG. 1) as shown in Reference Example. However, the sensitivity is not good at the salt concentration of 0.5M and, as to the salt concentration of 0.1 to 0.4M, the calibration curve is not suitable for routine tests because it is a curved line. The reason why the curved line is not suitable for routine tests is that, although it is convenient for routine tests to prepare a calibration curve by taking only 2 points, for example, at 0 and 100% of ATIII activities, many further points are required for preparing a calibration curve in the case of the curved line as U.S. Pat. No. 4,918,001 (Apr. 17, 1990). In addition, in U.S. Pat. No. 4,918,001 (Apr. 17, 1990), since the reaction time course is not linear as seen from FIG. 1 of U.S. Pat. No. 4,918,001 (Apr. 17, 1990), only limited automatic analyzers can be used. For example, Hitachi 7150 cannot be used. Average CV of simultaneous reproducibilities using normal specimens and abnormal specimens at respective salt concentrations of 0.2M, 0.3M and 0.4M (n=5) is 7.7% (Reference Example) and this is a problem for applying the method to routine tests in accuracy. Because of these reasons, the method of U.S. Pat. No. 4,918,001 (Apr. 17, 1990) is not desired for a routine determination method of ATIII.

In addition, there is no suggestion of avoidance of the influence of HCII in U.S. Pat. No. 4,918,001 (Apr. 17, 1990). Furthermore, in the present invention, it is essential to react a sample with thrombin in advance and the order of reaction is of importance. In view of these, the method disclosed in U.S. Pat. No. 4,918,001 (Apr. 17, 1990) is different from the method of the present invention.

Samples, reagents and the like used in the determination method of the present invention will be illustrated hereinbelow.

Firstly, samples to be used in the determination method of the present invention are, usually, plasma. Blood is collected from a subject and plasma is separated therefrom according to a conventional method.

In the determination method of the present invention, thrombin derived from human being, cattle, horse, goat and the like can be used.

As chromogenic substrates which develop color by a recation with thrombin, S-2238 (H-D-Phe-Pip-Arg-pNA), Spectrozyme-TH (H-D-CHT-Ala-Arg-pNA), Chromozym-TH (Tos-Gly-Pro-Arg-pNA), CBS-34-47 (H-D-CHG-But-Arg-pNA), 2AcOH-H-D-HHT-Ala-Arg-pNA and the like have been known and any of these thrombin substrates can be used.

As salts, neutral salts such as sodium chloride, potassium chloride and the like are preferred. These reagents including heparin are commercially available. Heparin and a salt may be separated from a thrombin reagent. However, it is desired to incorporate them with a thrombin reagent. If necessary, pH's of a thrombin reagent and a chromogenic substrate reagent are adjusted. As a buffer for adjusting pH, there are tris, phosphate, barbital, imidazole, veronal, glycylglycine, BES, MOPS, TES, HEPES, TAPSO, TAPS and the like. These buffers are also commercially available.

Concentrations of respective reagents can be suitably selected. However, desirably, the concentration of thrombin in a final reaction mixture is 0.01 to 10 NIHU/ml, preferably, 0.2 to 2 NIHU/ml. Desirably, the concentration of the chromogenic substrate in a final reaction mixture is 0.01 to 5 mM, preferably, 0.1 to 0.5 mM. Desirably, the concentration of heparin in a mixture of a sample and thrombin is 0.02 to 100,000 U/ml, preferably, 1 to 1,000 U/ml. Desirably, the salt concentration in a mixture of a sample and thrombin is more than 0.20M and up to 0.90M, preferably, 0.25M to 0.60M, more preferably, 0.35M to 0.60M. The pH's of a mixture of a sample and thrombin and a final reaction mixture are adjusted with a buffer, desirably, in the range of 6.0 to 10.0, preferably, 7.5 to 8.5. Desirably, its concentration is 0.005 to 1.0M, preferably, 0.02 to 0.1M.

In the determination method of the present invention, various materials can be suitably added to a thrombin reagent and a chromogenic substrate reagent so as to maintain properties and quality of the reagents, to facilitate the production thereof. Examples thereof include saccharides; amino acids; proteins such as albumin and the like; amine compounds such as monoethylamine; and other materials such as polyethylene glycol, glycerol in addition to chelating reagents such as EDTA, EGTA; anti-fibrinolytic reagents such as epsilon aminocaproic acid, tranexamic acid, aprotinin; heparin inhibitors such as polybrene, protamine; preservatives such as sodium azide, gentamicin sulfate, thimerosal; and surfactants such as Triton X-100, Tween 20.

An embodiment of the operation in the determination method of the present invention is illustrated hereinbelow.

Firstly, a sample and a thrombin reagent is mixed. Alternatively, a sample may be mixed with a thrombin reagent containing heparin. In this stage, a salt may be contained in either or both of thrombin reagent and reagent containing heparin or, in the case of a diluted sample, in a sample.

The mixture is incubated at 15° to 50° C., preferably, 30° to 40° C. for a given time, e.g., 0.5 to 20 minutes, preferably, 1 to 5 minutes. By this incubation for a given time, ATIII in the sample is reacted with thrombin.

Then, a chromogenic substrate reagent is added and a color developed from the chromogenic substrate according to the remaining thrombin activity is measured. The measurement is carried out either by a rate measurement wherein the change of absorbance per time is measured or by an end point measurement wherein a reaction stopping solution is added after a given period of time. By comparing the value measured with a value obtained by using a standard sample, ATIII activity is determined. For the determination with an automatic analyzer, a rate measurement is preferred. For an end point measurement, in general, 10 to 50% acetic acid or 10 to 20% citric acid solution is used as the reaction stopping solution. In the method of the present invention, 1 to 50 μl, preferably, 3 to 10 μl of a sample is used per 1 ml of a final reaction mixture.

Furthermore, the present invention provides an improved reagent kit wherein a salt is included in addition to a known reagent kit comprising thrombin, heparin and a chromogen substrate in such an amount that the salt concentration in a reaction mixture of a sample and thrombin becomes more than 0.20M and up to 0.90M.

The reagent kit for the determination of ATIII activity of the present invention can be a mixture of constituent reagents or an assembly of respective constituent reagents. The mixture of constituent reagents or respective constituent reagents can be in the form of a solution wherein the constituent reagent(s) together with an excipient are dissolved in distilled water or a buffer solution in such a concentration that the desired concentration in a reaction mixture can be obtained, and which can be directly served to use in the determination as it is, or in the form of a concentrated solution which is diluted to the desired concentration upon use, or in the form of a lyophilized product according to conventional methods. Among them, a lyophilized product is usually employed and, upon use, it is restored with distilled water or a buffer solution. Furthermore, respective constituent reagents can be in the same forms or different forms.

In any case, the amount of a salt in the reagent kit is selected from such a range that the salt concentration in a reaction mixture of a sample and thrombin exceeds 0.20M and not more than 0.9M.

The following Reference Example and Examples further illustrate the present invention in detail.

REFERENCE EXAMPLE

The reference example was carried out according to the method disclosed in Example 1 of U.S. Pat. No. 4,918,001

(Apr. 17, 1990). To a specimen (20 μl) was added 2 mM chromogenic substrate S-2238 (40 μl) and then to the mixture was added a solution (200 μl) of 0.1M tris-HCl buffer containing thrombin (1 NIHU/ml) and heparin (2.5 U/ml) (thrombin reagent, pH 8.2). After 15 seconds up to 90 seconds, the change of absorbance at 405 nm was measured at 37° C. For measurement, an automatic analyzer COBAS FARA II (manufactured by Roche, Switzerland) was used. Sodium chloride was added to the thrombin reagent in a concentration of 0.1M, 0.2M, 0.3M, 0.4M or 0.5M. A calibration curve was prepared by using a commercially available normal plasma Caliplasma Index 100 (manufactured by bioMerieux S.A., France) as a standard, physiological saline solution for diluting the specimen (ATIII activity of 25, 50 or 75%) and physiological saline solution itself as the specimen for 0% of ATIII activity. In addition, 100% of ATIII activity (normal specimen) and 50% of ATIII activity (abnormal specimen) were measured 5 times at respective salt concentrations and ATIII activities were calculated from the calibration curve to evaluate simultaneous reproducibility.

As shown in FIG. 1, the calibration curve was prepared between sodium chloride concentrations of 0.1M and 0.5M. However, the sensitivity at the concentration of 0.5M was not preferred and the calibration curve was not linear between the concentrations of 0.1M and 0.4M. Simultaneous reproducibility at sodium chloride concentration of 0.1M was 7.2 to 12.7% of CV and the average CV of simultaneous reproducibilities of respective measurements at sodium chloride concentrations of 0.2 to 0.4M was 7.7%.

The calibration curve was not linear, reproducibility was as low as about 7% and, as shown by FIG. 1 of U.S. Pat. No. 4,918,001 (Apr. 17, 1990), the reaction time course was non-linear. This is therefore not desirable for using as routine tests. Thus, it has been proved that the order of operation is of importance.

EXAMPLE 1

Preparation of HCII fraction

Barium sulfate (10 g) was added to human normal plasma. (40 ml, purchased from Nippon Biological Material Center). After stirring the mixture (for 15 minutes), it was centrifuged at 3,000 r.p.m. for 15 minutes to separate a supernatant. The supernatant was passed through a column (plastic injection cylinder 35 ml manufactured by Nipro) of heparin agarose equilibrated with 20 mM tris-HCl buffer (pH 7.3) (25 ml, Type II manufactured by Sigma, U.S.A.) to adsorb and remove ATIII. The effluent fraction was collected. Furthermore, for removing ATIII completely, the recovered fraction was again passed through the same column and the effluent fraction was collected. The effluent fraction was concentrated to about 5 to 6 times with Centriprep-10® (manufactured by Amicon, U.S.A.) to obtain HCII fraction.

EXAMPLE 2

Bovine thrombin (a constituent reagent of a fibrinogen kit manufactured by bioMerieux S.A. of France) was dissolved with 50 mM tris-HCl buffer (pH 8.4) containing 3 U/ml of heparin, 7.5 mM EDTA and 0.20 to 0.60M sodium chloride to bring the concentration to 3 NIHU/ml (thrombin reagent). A chromogenic substrate, 2AcOH-H-D-HHT-Ala-Arg-pNA (a constituent reagent of a ATIII determination kit (ATIII Chrom) manufactured by bioMerieux S.A.) was dissolved with distilled water (1.4 mM) to obtain a substrate reagent. A calibration curve was prepared by using commercially available normal plasma, Caliplasma Index 100 (manufactured by bioMerieux S.A.) and diluting with physiological saline solution to obtain 0% (only physiological saline solution), 25%, 50% and 100% (without dilution) of ATIII activities. By using the HCII fraction obtained in Example 1 as a specimen, the measurement was carried out and ATIII activity was determined from the calibration curve to evaluate the influence of HCII. For the measurement, the automatic analyzer, COBAS FARA, was used. In the determination method of the present invention, the thrombin reagent (200 μl) was added to the specimen (2 μl) and the mixture was incubated at 37° C. for 3 minutes. Then, the substrate reagent (100 μl) was added thereto and, from 20 to 90 seconds after the addition, the absorbance at 405 nm was measured to determine the change of absorbance per 1 minute.

As a result of the study of the influence of HCII on ATIII determination, a great influence was observed at the salt concentration of 0.20M which was employed in a conventional method, while no influence of HCII was observed at a salt concentration of not less than 0.3M.

In addition, the influence of HCII was studied in more detail at sodium chloride concentrations of 0.20 to 0.30M. The results are shown in Table 1. At the salt concentration of 0.22M, about 40% of the influence in a conventional method was avoided and, at the salt concentration of 0.24M, about 60% influence avoidance effect was observed. At the salt concentration of 0.26M, about 90% influence avoidance effect was observed and, at the salt concentration of 0.30M, no influence of HCII was observed. By adjusting the salt concentration of the reaction mixture of the sample and the thrombin reagent, HCII influence avoidance effect was observed. It has been found that ATIII can be determined accurately by utilizing this HCII influence avoidance effect.

TABLE 1

HCII Influence Avoidance Effect

| | | Concentration of NaCl | | | | | |
|---|---|---|---|---|---|---|---|
| | M | 0.20 | 0.22 | 0.24 | 0.26 | 0.28 | 0.30 |
| ATIII activity (%) | | 36 | 22 | 14 | 4 | 2 | 0 |
| HCII influence (%) | | (100) | 61 | 31 | 11 | 6 | 0 |

EXAMPLE 3

According to the method of Example 2, the determination was carried out and a calibration curve was prepared with respect to the salt concentration by using a thrombin reagent containing 2 NIHU/ml of thrombin and using specimens for preparing the calibration curve having ATIII activities of 0, 25, 50, 75 and 100%. Furthermore, 100% of ATIII activity (normal specimen) and 50% (abnormal specimen) were measured 5 times at the respective salt concentrations and ATIII activities were determined from the calibration curve to estimate simultaneous reproducibility. The calibration curve at the respective salt concentrations is shown in FIG. 2.

At a salt concentration of less than 0.30M, in the case of 100% of ATIII activity, about 90% of thrombin added was inhibited and the linearity of the calibration curve was maintained at up to 75% of ATIII activity. On the other hand, at the salt concentration of 0.40M, inhibition of thrombin was about 50% and, at the salt concentration of 0.50M, inhibition of thrombin was about 15%. The linearity was maintained up to 100% of ATIII activity. However, under these conditions, desired sensitivities were not obtained at 0.50M and 0.60M. The average CV of simultaneous reproducibilities of respective measurements at 0.20 to 0.40M was 2.3%. This CV corresponds to the accuracy of measurement suitable for using as routine tests.

In addition, according to the same method, proportions of remaining thrombin activities to 100% of ATIII activity were calculated at the salt concentrations between 0.30M and 0.40M. The results are shown in Table 2.

As the salt concentration increases, the proportion of remaining thrombin activity increases.

These results show that more amount of a specimen can be used at a high salt concentration and that the amount of thrombin activity to be added as a reagent can be reduced.

TABLE 2

Salt Concentration and Proportion of Remaining Thrombin

| ATIII | M | Concentration of NaCl | | | | | |
|---|---|---|---|---|---|---|---|
| | | 0.30 | 0.32 | 0.34 | 0.36 | 0.38 | 0.40 |
| 0% (ΔOD/min) | | 1.275 | 1.273 | 1.319 | 1.284 | 1.281 | 1.316 |
| 100% (ΔOD/min) | | 0.096 | 0.176 | 0.280 | 0.344 | 0.593 | 0.689 |
| Remaining thrombin (%) | | 7.5 | 13.8 | 21.2 | 26.8 | 46.3 | 52.3 |

EXAMPLE 4

According to the method of Example 3, the relationship between salt concentration and its calibration curve in the presence of a very high concentration of heparin such as 1,000 U/ml was studied. The results are shown in FIG. 3. In view of these results and the results in Example 3, the salt concentration and heparin concentration have a relation to each other and, in general, it is understood that a higher concentration of heparin is required at a higher salt concentration, but a preferred heparin concentration is present with respect to a given salt concentration. The results show that, even for a salt concentration of higher than 0.50M at which the sensitivity was not preferred in Example 3, a salt concentration of 0.50 to 0.90M can be employed by suitably selecting the concentration of heparin.

EXAMPLE 5

The ATIII activity determination kit of the present invention was obtained by combining a thrombin reagent composed of 50 mM tris-HCl buffer solution (pH 8.4) containing 1.0 NIHU/ml of thrombin, 3 U/ml of heparin, 7.5 mM EDTA and 0.4M sodium chloride with a substrate reagent composed of 1.4 mM chromogenic substrate, 2AcOH-H-D-HHT-Ala-Arg-pNA.

As described hereinbefore, according to the method of the present invention, the influence of HCII in ATIII determination can be avoided by such a very simple method that a salt concentration in a reaction mixture of a conventional ATIII determination method is increased with minimum economical burden. The amount of thrombin to be used can be reduced and the method of the present invention can accurately, easily and simply determine ATIII within a very short period of time without dilution of a sample and exceeding the measurable limit of absorbance and is readily applicable to an automatic analyzer. Thus, the method of the present invention is useful for using as routine tests.

What is claimed is:

1. A method for the determination of antithrombin III activity which comprises adding an excess amount of thrombin to a sample, reacting antithrombin III in the sample with the thrombin in the presence of heparin and a salt to form a reaction mixture, and then measuring a remaining throbin activity in the reaction mixture with a chromogenic substrate which develops a color by the reaction with thrombin, thereby indirectly determining the antithrombin III activity of the sample, the concentration of said salt in the reaction mixture being more than 0.20M to not more than 0.90M.

2. A reagent kit for the determination of antithrombin III activity without dilution of a sample, said kit comprising (a) a thrombin reagent containing heparin, and a salt, and (b) a chromogenic substrate reagent, the amount of the salt in (a) being such that the salt concentration in a reaction mixture of a predetermined volume of sample and a predetermined volume of the thrombin reagent becomes more than 0.20M and up to 0.90M.

3. A reagent kit for the determination of antithrobin III activity with dilution of a sample which comprises:

(a) a sample-dilution solution, (b) a thrombin reagent, and (c) a chromogenic substrate reagent, wherein heparin and a salt are contained in the sample-dilution solution or the thrombin reagent or both the sample-dilution solution and the thrombin reagent, the amount of the salt being such that the concentration of said salt in a mixture of respective predetermined volumes of the sample, the sample-dilution solution, and the thrombin reagent becomes more than 0.20M and up to 0.90M upon formation of said mixture.

4. A method according to claim 1, wherein the concentration of said salt is not less than 0.25M to 0.60M.

5. A method according to claim 1, wherein the concentration of said salt is not less than 0.35M to 0.60M.

6. A method according to claim 1, wherein the sample comprises plasma.

7. A method according to claim 1, wherein the salt is selected from the group consisting of sodium chloride and potassium chloride.

8. A method according to claim 1, wherein the sample is not diluted prior to adding the thrombin to the sample.

9. A method according to claim 1, wherein the concentration of thrombin in the reaction mixture is 0.01 to 10 NIHU/ml.

10. A method according to claim 1, wherein the concentration of the chromogenic substrate reagent in the reaction mixture is 0.01 to 5 mM.

11. A method according to claim 1, wherein the concentration of heparin in the reaction mixture is 0.02 to 100,000 U/ml.

12. A method according to claim 1, wherein the pH of the reaction mixture is in a range of 6.0 to 10.0.

13. A method according to claim 1, wherein the thrombin added to the sample also includes heparin and the salt.

14. A method according to claim 1, wherein the heparin, and salt are added after the thrombin is added to the sample.

* * * * *